United States Patent
Chang

(10) Patent No.: US 7,922,538 B2
(45) Date of Patent: Apr. 12, 2011

(54) SOUND SOCKET CONNECTOR WITH BUILT-IN SOUND PROCESSING CAPABILITY

(76) Inventor: Nai-Chien Chang, Sanchong (TW)

( * ) Notice: Subject to any disclaimer, the term of this patent is extended or adjusted under 35 U.S.C. 154(b) by 0 days.

(21) Appl. No.: 12/637,083

(22) Filed: Dec. 14, 2009

(65) Prior Publication Data

US 2010/0203744 A1    Aug. 12, 2010

(30) Foreign Application Priority Data

Feb. 12, 2009  (TW) .............................. 98202024 U

(51) Int. Cl.
*H01R 13/66* (2006.01)
(52) U.S. Cl. .................................... 439/620.16; 439/577
(58) Field of Classification Search ................... 439/79, 439/541.5, 540.1, 620.15–620.19, 577, 63, 439/76.1
See application file for complete search history.

(56) References Cited

U.S. PATENT DOCUMENTS

| | | | |
|---|---|---|---|
| 5,491,774 A * | 2/1996 | Norris et al. .................... 704/270 |
| 6,478,616 B1 * | 11/2002 | Yeh ............................ 439/541.5 |
| 6,508,665 B1 * | 1/2003 | Yeh ............................ 439/541.5 |
| 6,545,890 B2 * | 4/2003 | Pitzele .......................... 363/147 |
| 6,691,196 B2 * | 2/2004 | Mills et al. ..................... 710/301 |
| 6,863,557 B2 * | 3/2005 | Mills et al. ..................... 439/377 |
| 7,029,329 B1 * | 4/2006 | Huang ...................... 439/607.01 |
| 7,156,699 B1 * | 1/2007 | Liu ........................... 439/607.55 |
| 7,291,018 B2 * | 11/2007 | Nishizawa et al. .............. 439/60 |
| 7,300,314 B2 * | 11/2007 | Kim ............................... 439/630 |
| 7,341,488 B2 * | 3/2008 | Yang et al. ................ 439/607.35 |
| 2002/0037668 A1 * | 3/2002 | Tseng et al. ................... 439/660 |
| 2003/0009249 A1 * | 1/2003 | Loeb et al. ....................... 700/94 |
| 2003/0054703 A1 * | 3/2003 | Fischer et al. ................. 439/894 |
| 2004/0117521 A1 * | 6/2004 | Chen et al. ....................... 710/62 |
| 2004/0180574 A1 * | 9/2004 | Liu ............................. 439/541.5 |
| 2005/0232445 A1 * | 10/2005 | Vaudrey et al. ............... 381/109 |
| 2006/0079114 A1 * | 4/2006 | Tsai .............................. 439/394 |
| 2008/0166907 A1 * | 7/2008 | Sanford et al. ................ 439/345 |

* cited by examiner

*Primary Examiner* — Neil Abrams
*Assistant Examiner* — Harshad C Patel
(74) *Attorney, Agent, or Firm* — Chun-Ming Shih; HDLS IPR Services

(57) ABSTRACT

A sound socket connector with built-in sound processing capability includes a base, a sound circuit board, a metallic casing and a rear cover. The base has a front surface and a rear surface. The front surface has a plurality of sound input ports. The rear surface has a plurality of outward-extending electric-conductive pins at positions corresponding to those of the sound input ports. One end of the sound circuit board has a plurality of perforations. The electric-conductive pins pass through the perforations to be electrically connected to the sound circuit board. The other end of the sound circuit board is electrically connected with electric-conductive terminals. The electric-conductive terminals are electrically connected to a mother board. A decoder, a sound processor and a wireless module are electrically connected between the perforations and the electric-conductive terminals.

7 Claims, 4 Drawing Sheets

SOUND SOCKET CONNECTOR WITH BUILT-IN SOUND PROCESSING CAPABILITY

BACKGROUND OF THE INVENTION

1. Field of the Invention

The present invention relates to a connector, and in particular to a sound socket connector with built-in sound processing capability.

2. Description of Prior Art

The input/output panel of a current computer is provided with a sound socket connector having a plurality of ports. The sound socket connector can be externally connected to an earphone or speaker, so that a user can listen to the music played by the computer or talk to someone at a long distance by means of the Internet.

The current sound socket connector having a plurality of ports is only used to transmit audio signals, but the processing of sound is performed by a sound card. In this way, the user can listen to the music. Recently, with the continuous advancement of science and technology, the sound card has been integrated with a mother board of the computer, so that more space in the computer casing can be used for the heat dissipation of electronic components on the mother board. However, such an arrangement unfavorably increases the difficulty in designing and manufacturing the mother board of the computer.

Therefore, it is an important issue for the present Inventor to solve the above-mentioned problems.

SUMMARY OF THE INVENTION

The present invention is to integrate the circuit of a sound card of with a sound socket connector in a computer, thereby simplifying the design and manufacture of the mother board of the computer and reducing the volume of the mother board. With this arrangement, the sound socket connector also has a capability of processing sound.

The present invention is to provide a sound socket connector with built-in sound processing capability, including:

a base having a front surface and a rear surface, the front surface having a plurality of sound input ports, the rear surface having a plurality of outward-extending electric-conductive pins at positions corresponding to those of the sound input ports;

a sound circuit board with its one end having a plurality of perforations, the electric-conductive pins passing through the perforations to be electrically connected to the sound circuit board, the other end of the sound circuit board being electrically connected with electric-conductive terminals, the electric-conductive terminals being electrically connected to a mother board, a decoder, a sound processor and a wireless module being electrically connected between the perforations and the electric-conductive terminals;

a metallic casing covering the base and having a front panel, the front panel having a plurality of holes for displaying the sound input ports, both sides of the front panel extending to form two side plates, the side plates having fixed pins; and a rear cover assembled within the metallic casing and located behind the base.

DETAILED DESCRIPTION OF THE INVENTION

The characteristics and technical contents of the present invention will be described with reference to the accompanying drawings. However, the drawings are illustrative only but not used to limit the present invention.

Figure 1:
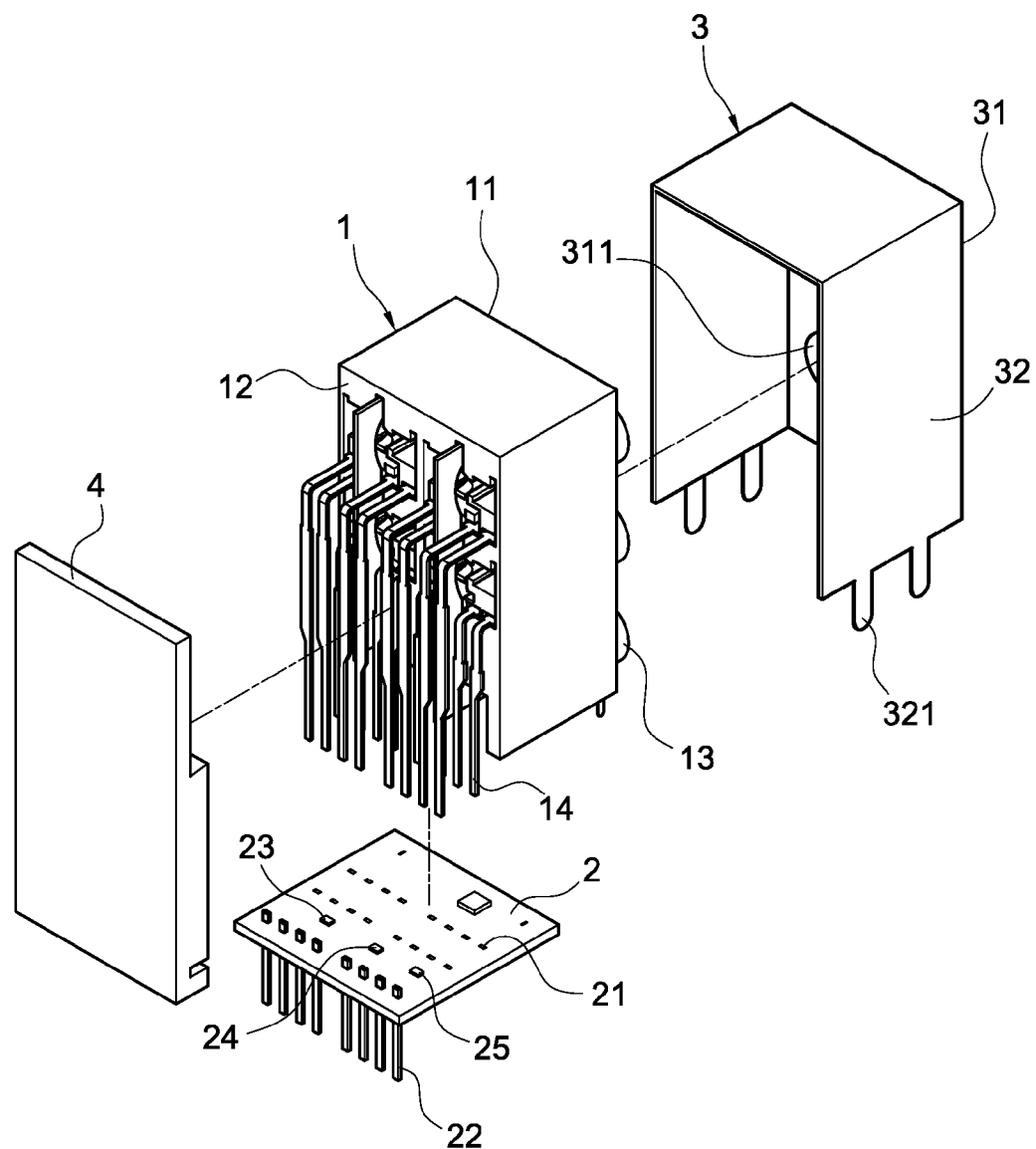
FIG. 1 is an exploded perspective view showing a sound socket connector of the present invention.
Figure 2:
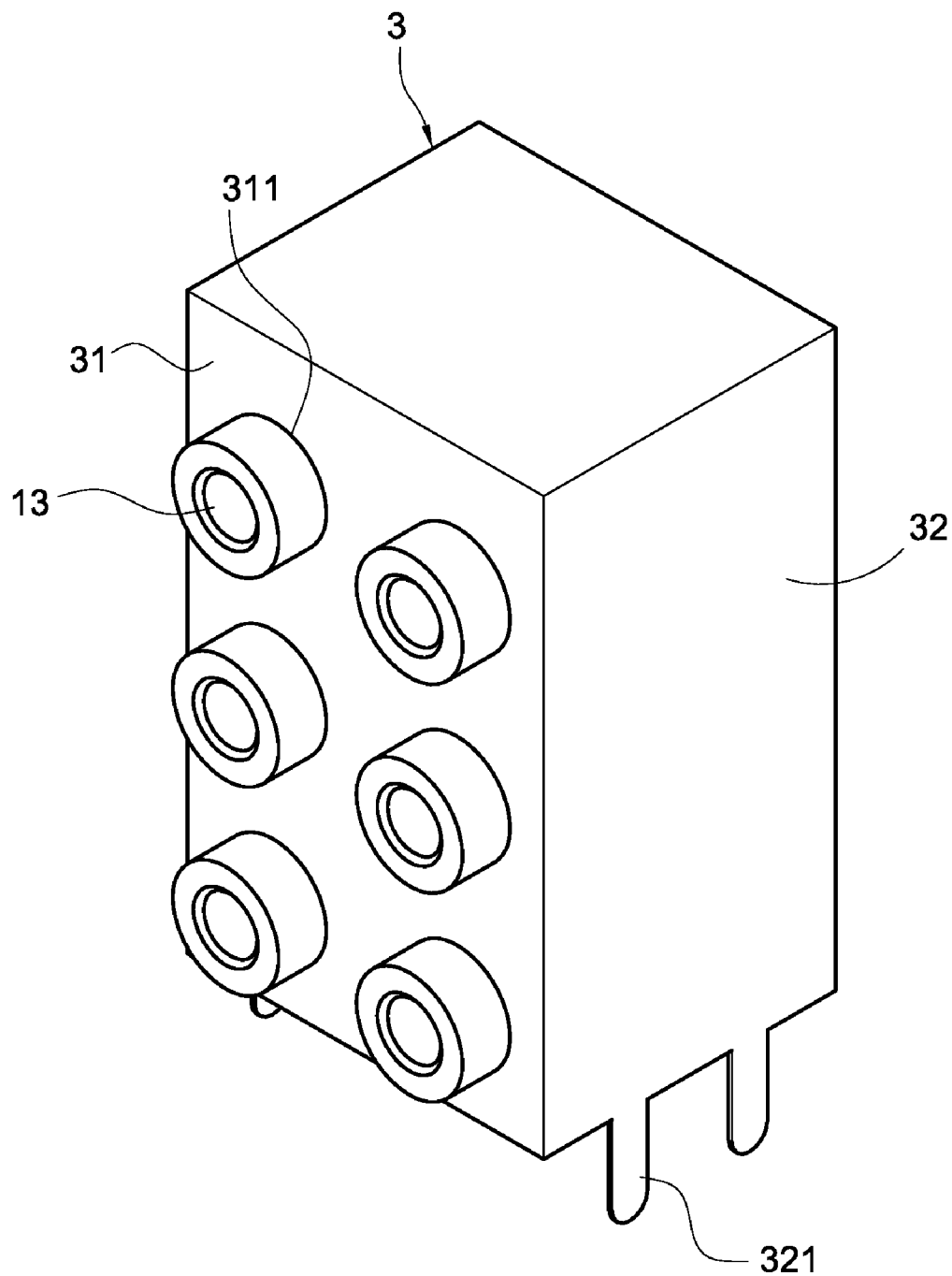
FIG. 2 is a perspective view showing the external appearance of the sound socket connector of the present invention.

Please refer to FIGS. 1 and 2. FIG. 1 is an exploded perspective view showing a sound socket connector of the present invention, and FIG. 2 is a perspective view showing the external appearance of the sound socket connector of the present invention. The present invention provides a sound socket connector with built-in sound processing capability, which includes a base 1, a sound circuit board 2, a metallic casing 3, and a rear cover 4.

The base 1 has a front surface 11 and a rear surface 12. The front surface 11 has a plurality of sound input ports 13. The rear surface 12 has a plurality of outward-extending electric-conductive pins 14 at positions corresponding to those of the sound input ports 13. After a plug of an earphone or speaker (not shown) is inserted into the sound input port 13, an electric-conductive portion of the plug is brought into electrical contact with one end of the electric-conductive pin 14.

One end of the sound circuit board 2 has a plurality of perforations 21. The electric-conductive pins 14 pass through the perforations 21 to be electrically connected to the sound circuit board 2. The other end of the sound circuit board 2 is electrically connected with electric-conductive terminals 22. A decoder 23, a sound processor 24 and a wireless module 25 are provided on the sound circuit board 2 between the perforations 21 and the electric-conductive terminals 22. In the drawings, the decoder 23 is a multi-channel decoder (such as Dolby digital 5.1, DTS 5.1). The sound processor 24 is configured to convert a digital signal into an analog signal, improving its sound quality, and amplifying the signal. The wireless module 25 is configured to receive the audio signal received by a wireless microphone.

The metallic casing 3 is configured to cover the base 1 and has a front panel 31. The front panel 31 has a plurality of holes 311 for displaying the sound input ports 13. Further, both sides of the front panel 31 extend to form two side plates 32. The side plate 32 has fixed pins 321 fixed to a mother board (not shown). The metallic casing 3 is assembled on the base 1 for protecting against electro-magnetic interference.

The rear cover 4 is assembled within the metallic casing 3 and located behind the base 1 for protecting the electro-conductive pins 14 of the base 1 from suffering damage.

Figure 3:
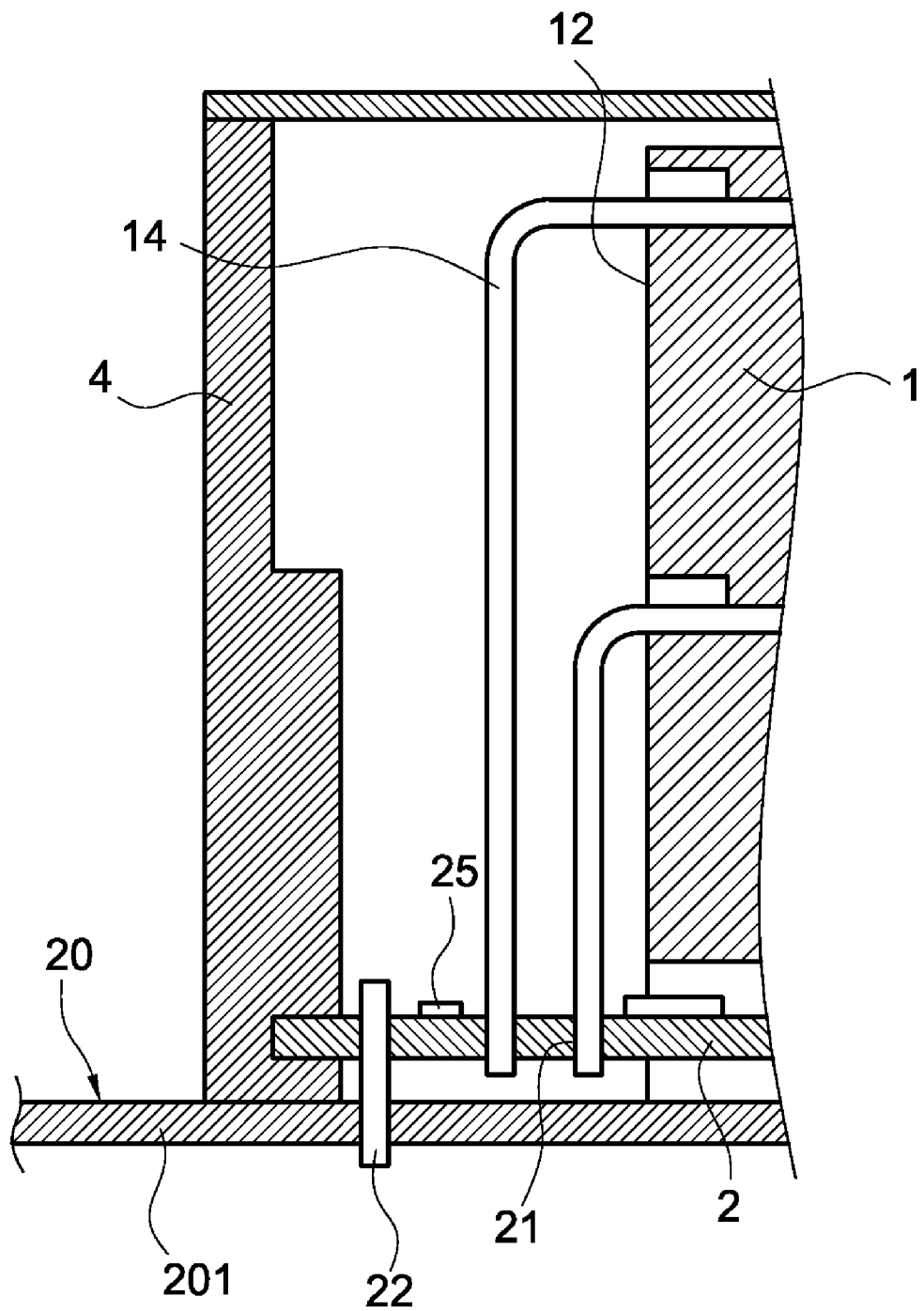
FIG. 3 is a schematic view showing an operating state of the sound socket connector of the present invention.
Figure 4:
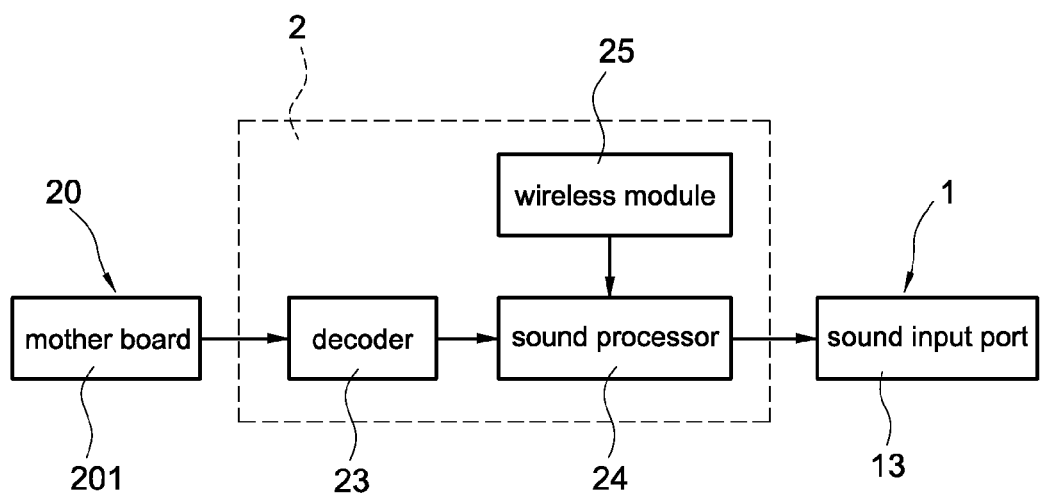
FIG. 4 is a block view showing the circuit of the sound socket connector of the present invention.

Please refer to FIGS. 3 and 4. FIG. 3 is a schematic view showing an operating state of the sound socket connector of the present invention, and FIG. 4 is a block view showing the circuit of the sound socket connector of the present invention. As shown in these figures, the sound socket connector of the present invention is electrically connected to a mother board 201 of an electronic device 20. After the mother board 201 of the electronic device 20 outputs an audio signal, the audio signal is decoded by the decoder 23. Then, the decoded signal is transmitted to the sound processor 24. After the signal is subjected to digital/analog conversion, improvement in sound quality, and amplification of the signal by the sound processor 24, the processed signal is transmitted to the sound input port 13. At this time, the user inserts a plug of an earphone or speaker into the sound input port 13, so that the user can listen to pretty sound.

When the user wants to sing a song, he/she only needs to take a wireless microphone and sing to it. At this time, the audio signals received by the wireless microphone are transmitted to the wireless module 25 and then processed by the sound processor 24, so that the user can listen to pretty sound from the earphone or the speaker.

Although the present invention has been described with reference to the foregoing preferred embodiments, it will be understood that the invention is not limited to the details thereof. Various equivalent variations and modifications can still occur to those skilled in this art in view of the teachings of the present invention. Thus, all such variations and equivalent modifications are also embraced within the scope of the invention as defined in the appended claims.

What is claimed is:

1. A sound socket connector with built-in sound processing capability, electrically connected to a mother board of an electronic device and including:
   a base having a front surface and a rear surface, the front surface having a plurality of sound input ports, the rear surface having a plurality of outward-extending electric-conductive pins at positions corresponding to the sound input ports;
   a sound circuit board with its one end having a plurality of perforations, the electric-conductive pins passing through the perforations to be electrically connected to the sound circuit board, the other end of the sound circuit board being electrically connected with electric-conductive terminals, the electric-conductive terminals being electrically connected to the mother board, via a decoder electrically connected to the mother board and via a sound processor electrically connected to the decoder and the electric-conductive terminals, and a wireless module being electrically connected between the perforations and the electric-conductive terminals and being electrically connected to the sound processor.

2. The sound socket connector with built-in sound processing capability according to claim 1, wherein the decoder is a multi-channel decoder.

3. The sound socket connector with built-in sound processing capability according to claim 1, wherein the sound processor is configured to convert a digital signal into an analog signal, improving its sound quality, and amplifying the signal.

4. The sound socket connector with built-in sound processing capability according to claim 1, further including a metallic casing, the metallic casing being configured to cover the base.

5. The sound socket connector with built-in sound processing capability according to claim 4, wherein the metallic casing has a front panel, the front panel has a plurality of holes for displaying the sound input ports, both sides of the front panel extend to form two side plates, and the side plates have fixed pins.

6. The sound socket connector with built-in sound processing capability according to claim 1, wherein the decoder is capable of decoding an audio signal from the motherboard and transmitting a decoded signal to the sound processor, the sound processor capable of subsequently transmitting a processed signal to the sound input ports.

7. The sound socket connector with built-in sound processing capability according to claim 1, further comprising a wireless microphone, wherein an audio signal is transmitted from the wireless microphone to the wireless module, the wireless module capable of transmitting the audio signal to the sound processor, and the sound processor capable of subsequently sending a processed signal to the sound input ports.

* * * * *